United States Patent
Osman

(10) Patent No.: US 10,039,883 B2
(45) Date of Patent: Aug. 7, 2018

(54) PEN-TYPE INJECTOR WITH WINDOW ELEMENT

(71) Applicant: SANOFI-AVENTIS DEUTSCHLAND GMBH, Frankfurt am Main (DE)

(72) Inventor: Thomas Frederick Osman, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 414 days.

(21) Appl. No.: 14/389,570

(22) PCT Filed: Apr. 2, 2013

(86) PCT No.: PCT/EP2013/056854
§ 371 (c)(1),
(2) Date: Sep. 30, 2014

(87) PCT Pub. No.: WO2013/149980
PCT Pub. Date: Oct. 10, 2013

(65) Prior Publication Data
US 2015/0065960 A1   Mar. 5, 2015

Related U.S. Application Data

(60) Provisional application No. 61/666,274, filed on Jun. 29, 2012.

(30) Foreign Application Priority Data

Apr. 5, 2012  (EP) .................................. 12163485

(51) Int. Cl.
*A61M 5/24* (2006.01)
*A61M 5/31* (2006.01)
*A61M 5/142* (2006.01)

(52) U.S. Cl.
CPC ............ *A61M 5/24* (2013.01); *A61M 5/3129* (2013.01); *A61M 5/142* (2013.01);
(Continued)

(58) Field of Classification Search
CPC ...... A61M 5/24; A61M 5/3129; A61M 5/142; A61M 2005/3126; A61M 2205/583;
(Continued)

(56) References Cited

U.S. PATENT DOCUMENTS 533,575 A   2/1985  Wilkens
4,865,591 A  9/1989  Sams
(Continued)

FOREIGN PATENT DOCUMENTS

CA   2138528       12/1998
CA   2359375 A1    7/2000
(Continued)

OTHER PUBLICATIONS

International Search Report for Int. App. No. PCT/EP2013/056854, completed May 29, 2013.
(Continued)

*Primary Examiner* — Amber Stiles
(74) *Attorney, Agent, or Firm* — Fish & Richardson P.C.

(57) ABSTRACT

The present invention is directed to a housing for a drug delivery device. The housing comprises an outer shell with an aperture, an insert received within the aperture and a clamp attached to the outer shell. The insert has at least one recess which is engaged by a lug of the clamp to retain the insert within the aperture of the outer shell. The invention is further directed to a pen-type injector having such a housing.

12 Claims, 2 Drawing Sheets

(52) U.S. Cl.
CPC .............. *A61M 2005/3125* (2013.01); *A61M 2005/3126* (2013.01); *A61M 2205/19* (2013.01); *A61M 2205/583* (2013.01); *A61M 2205/585* (2013.01); *A61M 2207/00* (2013.01)

(58) Field of Classification Search
CPC ........ A61M 2207/00; A61M 2205/585; A61M 2205/19; A61M 2005/3125
See application file for complete search history.

(56) References Cited

U.S. PATENT DOCUMENTS

| | | | |
|---|---|---|---|
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,298,023 A | 3/1994 | Haber et al. | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michael | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,001,082 A * | 12/1999 | Dair ................ | A61M 5/31525 604/187 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,186,233 B2 | 5/2012 | Joung et al. | |
| 2002/0120235 A1 | 8/2002 | Enggaard | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2006/0153693 A1 | 7/2006 | Fiechter et al. | |
| 2007/0016143 A1 | 1/2007 | Miller et al. | |
| 2009/0275916 A1 | 11/2009 | Harms et al. | |
| 2010/0152667 A1* | 6/2010 | Kietzmann ....... | A61M 5/31551 604/189 |
| 2010/0274198 A1* | 10/2010 | Bechtold .......... | A61M 5/31551 604/189 |

FOREIGN PATENT DOCUMENTS

| | | |
|---|---|---|
| DE | 102007018696 | 10/2008 |
| EP | 0450905 | 10/1991 |
| EP | 0496141 A1 | 7/1992 |
| EP | 0897729 A2 | 2/1999 |
| EP | 0937471 A2 | 8/1999 |
| EP | 0937472 | 8/1999 |
| EP | 0937476 A2 | 8/1999 |
| EP | 1557189 | 7/2005 |
| EP | 1776975 A2 | 4/2007 |
| EP | 1920794 | 5/2008 |
| RU | 2438721 C2 | 1/2012 |
| WO | 9324160 A1 | 12/1993 |
| WO | 98/26834 | 6/1998 |
| WO | 9307922 A1 | 4/1999 |
| WO | 9938554 A1 | 8/1999 |
| WO | 01/10484 | 2/2001 |
| WO | 9230495 A2 | 4/2002 |
| WO | 02/092153 | 11/2002 |
| WO | 03080160 A1 | 10/2003 |
| WO | 2006084876 A1 | 8/2006 |
| WO | 2010/020311 | 2/2010 |
| WO | 2010/112558 | 10/2010 |

OTHER PUBLICATIONS

"Nokia E66 Bedienungsanleitung," Retrieved from the Internet: URL: http://nds1.nokia.com/phones/files/guides/Nokia_E66-1_UG_de.pdf [retrieved on Oct. 25, 2011].

English Translation of Official Action issued in Russian Patent Application No. 2014144315/14(071469) dated Feb. 9, 2017.

* cited by examiner

PEN-TYPE INJECTOR WITH WINDOW ELEMENT

CROSS REFERENCE TO RELATED APPLICATIONS

The present application is a U.S. National Phase Application pursuant to 35 U.S.C. § 371 of International Application No. PCT/EP2013/056854 filed Apr. 2, 2013, which claims priority to European Patent Application No. 12163485.1 filed Apr. 5, 2012 and U.S. Provisional Patent Application No. 61/666,274, filed Jun. 29, 2012. The entire disclosure contents of these applications are herewith incorporated by reference into the present application.

TECHNICAL FIELD

The present invention is directed to a housing for a drug delivery device. The invention further refers to a pen-type injector having such a housing. The housing may comprise an outer shell with an aperture, an insert received within the aperture and an additional member attached to the outer shell. Preferably, the additional member is a clamp which is snapped in place or locked within the outer shell.

For example in pen-type injectors or other drug delivery devices a housing may be any exterior housing, like a main housing or body, or any interior housing, like an insert or an inner body. Typically, the housing is designed to enable safe, correct and comfortable handling of the drug delivery device or any of its mechanisms. Usually, the housing is designed to house, fix, protect, guide and/or engage with any of the inner components of the drug delivery device, like a drive mechanism, a cartridge, a plunger, a piston rod or the like, by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may be dispensed.

BACKGROUND

A drug delivery device with such a housing is known for example from EP 1 920 794 B1. The housing of this known drug delivery device further comprises a window provided in an aperture of the housing. In pen-type injectors, it is advantageous to display the selected dose number which may be dialed on a number sleeve through a transparent lens or window located in the outer housing of the drug delivery device. The lens acts to magnify the selected dose value thus improving readability. It is important to ensure that the window or lens is robustly and reliably secured to the outer housing so that it does not become dislodged, or fall out during use of the drug delivery device. Achieving such a robust connection between a window or lens component and the housing may be a technical challenge.

One known example of achieving this is to form the components together as a two-shot molding. However, this requires an expensive tool and limits the material (usually polymers) and possible printing options for the parts. As an alternative, the window and the housing may be clipped together. However, to ensure that a robust connection is made, a reasonable depth of engagement is required between the parts to accommodate flexible clip features. This arrangement may complicate printing of the window or lens and may increase the overall size of the device. A further option could be to bond the parts together using an adhesive or double-sided tape. However, the use of adhesives and tape requires careful control in the production environment and can have significant cost and complexity implications.

SUMMARY

It is an object of the present invention to provide a housing and a pen-type injector which overcome the limitations of the above joining methods whilst providing a robust joint between the housing and an insert.

This is achieved by a housing according to claim 1 and by a pen-type injector with the features of claim 811. One aspect of the present invention is to provide a catch or locking device for securing an insert to a housing which is preferably activated during assembly of the housing or the drug delivery device. This is achieved by a further component, like a clamp, which is attached to the outer shell of the housing. This further component is provided with a lug or catch which engages a recess provided in the insert. In other words, joining of the insert within the outer shell of the housing is achieved by providing a notch or recess within the insert which is engaged by a lug or catch of a separate component which in turn is fixed to the outer shell of the housing.

Preferably the aperture is formed on a side surface of the outer shell. The shape of the aperture may substantially conform to the shape of the insert. The aperture may form an opening that extends perpendicular or substantially perpendicular to a longitudinal axial of the outer shell and/or the housing. The main insertion direction for the insert may then be from a radially outward direction with regard to said longitudinal axis. According to a further embodiment, the aperture may be a single piece opening or hole with a continuous inner wall surface. In other words, the aperture is not formed by assembly of two outer shell components having half-circled notches or the like that are put together to form an aperture. Instead the aperture is of closed shape.

Preferably the further component or clamp is permanently attached to the outer shell during assembly of the drug delivery device. However, it is also possible to retain the insert within the aperture of the outer shell by a component which is releasably attached to the outer shell. In the latter case, the engagement between the lug or catch of the further component and the insert should be such that unintended loss of the insert is avoided.

According to a preferred embodiment of the invention, the insert further has at least one tail or catch extending beneath the outer shell or into a recess formed within the outer shell. In this way, the insert is held within the outer shell, while the further component (clamp) mainly serves to lock the insert in place. As an alternative, the tail or catch of the insert is attached to a further component (instead of the outer shell itself) which is preferably permanently attached to the outer shell.

A robust connection between the insert and the outer shell may be achieved if the tail or catch of the insert is located at one side and the recess into which the lug or catch of the further component (clamp) engages is located at an opposite side of the insert. Thus, the insert is held from two opposite sides.

In the above described embodiment the insert is provided with a male feature like a tail or catch and a female feature like a notch or recess to lock the insert within the aperture of the outer shell. As an alternative, the insert may be provided only with male features which engage corresponding female features of the outer shell and/or components attached to the outer shell or vice versa, i.e. the insert has only female features engaging male features of the outer shell and/or components attached thereto.

For a tight fit of the insert in the aperture, the end or tip of the tail or catch may be grooved so that undesired movement of the insert especially in lateral direction is effectively prevented. The lug and/or catch of the insert and/or the further component may at least partly be elastic such that during assembly, the respective sections are given a level of pre-stress during installation thus eliminating play resulting from manufacturing tolerances.

A typical example of an insert is a translucent or transparent window allowing a user to view the selected dose number e.g. of a number sleeve provided within the housing. Preferably, the insert comprises a magnifying lens improving readability of the selected dose value. However, the invention is not limited to a widow insert. As an alternative, the insert may be a clip, an activating member or a tag with information, like the manufacturer's name or the name of a medicament. Further, the invention is not limited to embodiments with only one single insert.

According to a preferred embodiment of the present invention, the rear surface of the insert (the side facing towards the interior of the outer shell) is provided with a printing or marking. In this way, the window aperture can be neatly and accurately defined and dose number alignment markings can also be applied. This arrangement has the further advantage that the printed surfaces are not exposed and so will not be scratched or abraded in use.

Preferably the further component (clamp) which is attached to the outer shell is an inner housing component or a housing insert fixed to the outer shell. Typically an inner housing engages or interacts with inner components of the drug delivery device, in particular components of the drive mechanism like a dose dial element, a display element (number sleeve), a drive member and/or a clutch member.

To further increase the robustness of the connection between the insert and the outer shell, the outer shell may be provided with at least one ledge or protrusion extending into the aperture to support the insert. In other words, the insert may rest on preferably two opposite ledges whilst the above mentioned locking mechanism mainly serves to fix the insert on the outer shell. Preferably, at least one ledge is provided as a stepped portion or off-set provided at the edge or border of the aperture.

The insert may be a plate-like element and/or an element having a shape that is substantially smaller in height in a direction perpendicular to the longitudinal axis of the outer shell or housing when received in the aperture than it extends in length and/or width in a plane substantially parallel to said longitudinal axis. It has been proven effective if at least the lower or rear surface of the insert facing the interior of the outer shell has a shape conforming to the interior surface of the shell in the section comprising the aperture. The outer shape of the insert may have a rounded contour to minimize injuries and offer an appealing haptic.

The recess may be formed on a side surface of the insert, preferably the distal (i.e. directed to the needle end) side face. The side surface may extend substantially transversely with respect to the outer or front surface of the insert when the insert is received in the aperture. The side surface may also be characterized as the edge surface of the insert. To improve assembly conditions, the side surface may be stepped or have at least one step-like section such that the insert at least partly overlaps the edge of the aperture and is supported on the outer surface of the outer shell while also being able to be supported by the inner wall surface of the aperture and/or the further component (clamp) in lateral direction.

According to another aspect of the invention, over substantially the entire circumference of the insert, the side surface is in contact with an inner opening surface of the aperture. To ensure efficient space utilization, the side surface may be configured in terms of height such that it merely extends between the outer and inner surface of the outer shell when the insert is attached in the aperture. This may also provide for a smooth transition between the outer surface of the shell and the insert. However, for an improved firm seat of the insert, the side surface respectively the thickness of the insert in the edge sections of the insert may vary, especially at the recess and/or tail.

A pen-type injector according to the present invention may include a cartridge and a housing as mentioned above, wherein the outer shell of the housing encases or protects at least partly the cartridge and/or components of the drive mechanism for setting and administering a dose from the cartridge.

According to a preferred embodiment of the invention, the further component (clamp) of the housing is an inner housing component located at least in part within the outer shell, wherein the drive mechanism comprises a display element, like a number sleeve, located interposed between the outer shell and the inner housing component. In other words, the outer shell and the inner housing component (clamp) may be provided coaxially with respect to each other and further coaxially with respect to the display element. Preferably, the outer shell and/or the inner housing component engages or interacts with the display element and/or further components of the drive mechanism.

The pen-type injector of the present invention may be a single-use device or a reusable device. Preferably, the pen-type injector is a resettable injection device which allows to exchange an empty cartridge by a new cartridge and to reset the drive mechanism such that the pen-type injector may be reused for different cartridges. However, the pen-type injector and its housing may similarly be used in a device which has to be discarded if the cartridge is empty.

The cartridge of the pen-type injector may contain a medicinal product such as a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε and γ have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention will be described by a way of an example and with reference to the schematic drawings in which.

DETAILED DESCRIPTION

Figure 1:
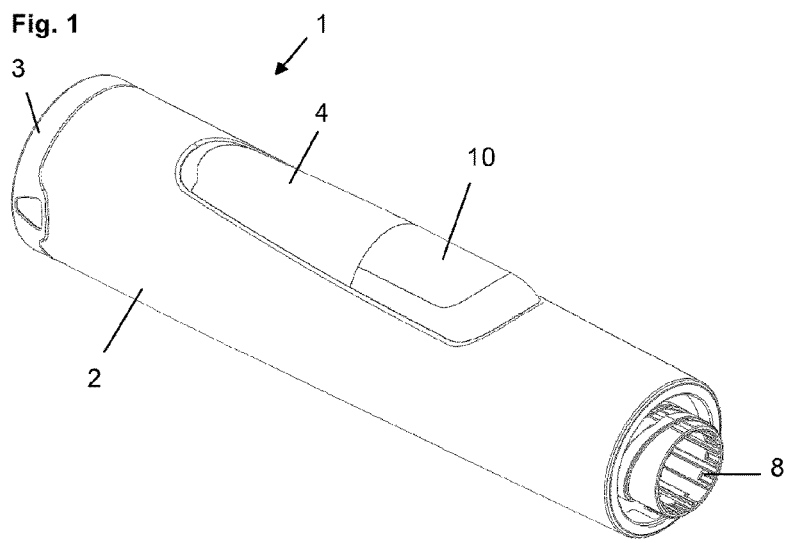
FIG. 1 shows a perspective view of a housing according to a first embodiment.
Figure 2:
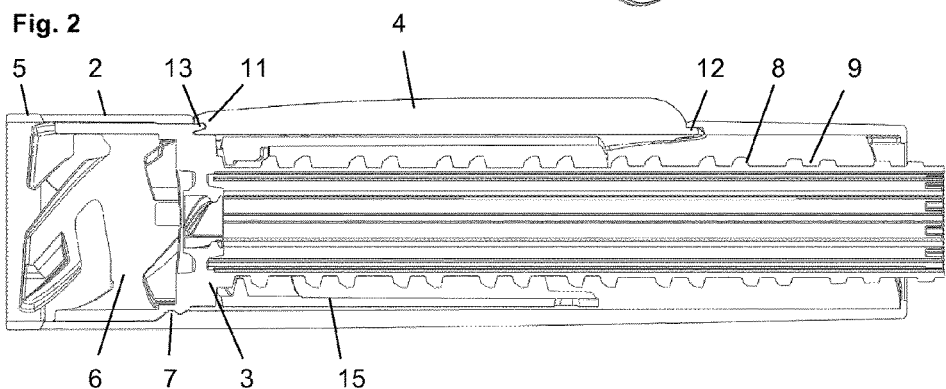
FIG. 2 shows a sectional view of the housing of FIG. 1.

The housing 1 depicted in FIGS. 1 and 2 mainly comprises an outer shell 2, a clamp in the form of an inner housing 3 and an insert 4 in the form of a magnifying lens or window. The outer shell 2 is a tubular element having an aperture in the form of a long hole into which the insert 4 is placed. The aperture is formed into the side surface of the outer shell 2. The outer dimension of the insert 4 corresponds to the shape of the aperture in the outer shell 2 such that the outer shell 2 is fully closed by insert 4. The housing has a proximal end (right hand side in FIG. 1) and an opposite distal end.

The inner housing 3 is a stepped tubular element on the distal side having a collar 5 which has an outer diameter which is identical to outer diameter of the outer shell 2 such that the collar 5 of the inner housing 3 forms a section of the outer surface of housing 1. The inner housing 3 further comprises an engagement area having an outer diameter which corresponds to the inner diameter of the outer shell 2 such that the engagement area 6 is received and fitted into outer shell 2. The engagement area 6 may be provided with a thread or bayonet features for attaching the cartridge holder to the inner housing 3. The engagement area 6 of the inner housing 3 further has a notch or groove which is engaged by a lug or ridge 7 provided on the inner surface of the outer shell 2 to snap the inner housing 3 into place within the outer shell 2. Thus, the inner housing 3 is firmly attached to the outer shell 2 such that at least any relative axial movement between the outer shell 2 and the inner housing 3 is prevented.

The inner housing 3 further has a sleeve like portion 8 with a reduced outer diameter which thus forms an annular space between the inner surface of the outer shell 2 and the outer surface of the inner housing 3. The sleeve-like part of the inner housing 3 may be provided with an external thread 9 for interaction with a display element like a number sleeve 15.

Figure 3:
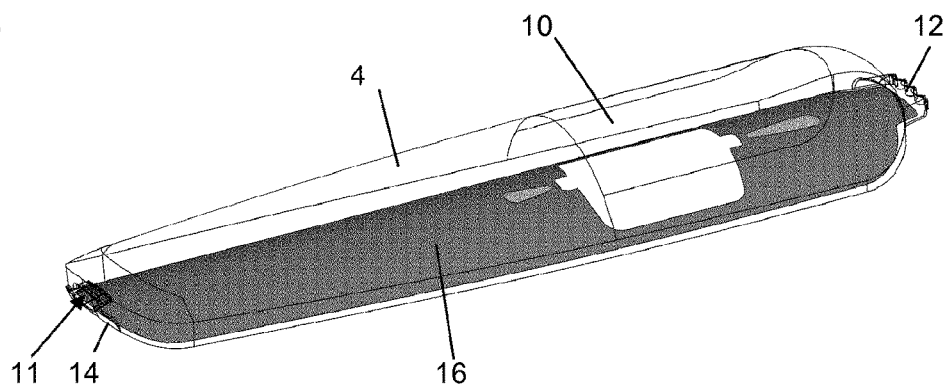
FIG. 3 shows a perspective view of an insert of the housing of FIG. 1.

The insert 4 is shown in FIG. 3 in more detail. According to an embodiment of the present invention the insert 4 is or may comprise a transparent window including a magnifying lens 10. In the embodiment shown in FIG. 3, the insert 4 has an elongate shape with a recess 11 provided on one side and a tail 12 or catch provided at an opposite side. The recess 11 is formed on a distal side surface of the insert 4. The tail 12 extends from the proximal side surface of the insert 3 in a direction opposite from the recess 11. The insert 4 may be lightly detented to the outer shell 2 for assembly purposes as indicated at the free end of tail 12 and the lip 14 on the opposite side. Further, the rear side of insert 4, i.e. the side facing towards the interior of outer shell 2, may be printed or marked as indicated by reference numeral 16. The tail 12 features a number of grooves formed into the tip end of the tail 12.

Figure 4:
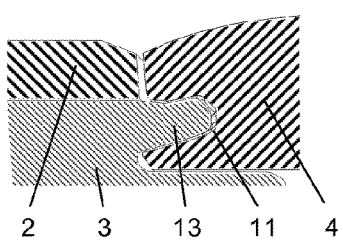
FIG. 4 shows an enlarged sectional detail of the housing of FIG. 1.
Figure 5:
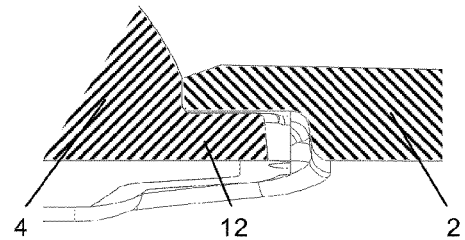
FIG. 5 shows a further enlarged sectional detail of the housing of FIG. 1.

The connection between insert 4 and outer shell 2 is depicted in FIGS. 4 and 5 in more detail. As can be taken from FIG. 5, tail 12 of insert 4 engages beneath the inner surface of outer shell 2. In addition, a lug 13 provided at the engagement area 6 of inner housing 3 engages recess 11 of insert 4. Further, insert 4 may be supported by ledges or protrusions (not shown) of outer shell 2 or inner housing 3.

According to the preferred example of the present invention, inner housing 3 is rigidly and permanently attached to the outer shell 2 during the assembly process of the drug delivery device. Insert 4 is retained within the aperture of outer shell 2. It is preferably located on ledges that extend along either side of the aperture in line with the main longitudinal axis of the device. These ledges prevent the insert from being pushed through the aperture and into outer shell 2. As mentioned above, the insert has a tail feature 12 on one end that locates beneath the inner wall of outer shell 2. At the opposite end of a tail feature 12, the recess 11 is formed in the insert. This recess 11 is designed to engage with a lug feature 13 of the inner housing 3, thus creating a robustly connected subassembly.

Differing from the embodiment depicted in FIGS. 1 to 5, insert 4 may only have male retaining features which engage corresponding female features of the outer shell 2 or further housing components or the insert may only have female retaining features, which engage corresponding male features of the outer shell 2 or further housing components. Further, additional retaining features may be provided for the insert.

The invention claimed is:

1. A housing for a drug delivery device, the housing comprising
   a tubular outer shell comprising open end faces and an aperture,
   an insert comprising an outer dimension that corresponds to a shape of the aperture of the outer shell, wherein the outer shell is closed when the insert is received within the aperture, and
   a clamp attached to the outer shell such that relative movement between the outer shell and the clamp is prevented, the clamp a separate component from the insert,
   the clamp comprising an engagement area for attaching a cartridge holder to the clamp;
   wherein the insert comprises at least one recess which is engaged by a lug of the clamp to retain the insert within the aperture of the outer shell,
   wherein the insert comprises at least one tail or catch extending beneath the outer shell or into a recess formed within the outer shell, and
   wherein the tail is located at a side of the insert opposite the side having the recess.

2. The housing according to claim 1, characterized in that the insert is a transparent or translucent window.

3. The housing according to claim 1, characterized in that the insert comprises a magnifying lens.

4. The housing according to claim 1, characterized in that the radially inwardly facing side of the insert is provided with a marking.

5. The housing according to claim 1, characterized in that the clamp is an inner housing component or a housing insert fixed to the outer shell.

6. The housing according to claim 1, characterized in that the outer shell is provided with at least one ledge extending into the aperture to support the insert.

7. The housing according to claim 1, characterized in that the insert is a plate-like element.

8. The housing according to claim 1, characterized in that the recess is formed on a side surface of the insert.

9. A pen-type injector, having a cartridge and a housing according to claim 1, with the outer shell of the housing at least partly encasing a drive mechanism for setting and administering a dose from the cartridge.

10. The pen-type injector according to claim 9, characterized in that the clamp of the housing is an inner housing component located at least in part within the outer shell, wherein the drive mechanism comprises a display element located interposed between the outer shell and the inner housing component.

11. The pen-type injector according to claim 9, wherein the cartridge contains a medicinal product.

12. The pen-type injector according to claim 9, characterized in that the pen-type injector is a resettable injection device.

* * * * *